(12) United States Patent
Deichmann et al.

(10) Patent No.: US 7,625,335 B2
(45) Date of Patent: Dec. 1, 2009

(54) METHOD AND APPARATUS FOR THREE-DIMENSIONAL OPTICAL SCANNING OF INTERIOR SURFACES

(75) Inventors: Nikolaj Deichmann, Kobenhavn O (DK); Tais Clausen, Kobenhavn O (DK); Rune Fisker, Kobenhavn N (DK); Christophe Vasiljev Barthe, Kobenhavn N (DK)

(73) Assignee: 3Shape ApS, Kobenhavn K (DK)

( * ) Notice: Subject to any disclaimer, the term of this patent is extended or adjusted under 35 U.S.C. 154(b) by 115 days.

(21) Appl. No.: 10/344,703

(22) PCT Filed: Aug. 24, 2001

(86) PCT No.: PCT/DK01/00561

§ 371 (c)(1),
(2), (4) Date: Apr. 10, 2003

(87) PCT Pub. No.: WO02/16867

PCT Pub. Date: Feb. 28, 2002

(65) Prior Publication Data

US 2003/0164952 A1 Sep. 4, 2003

(30) Foreign Application Priority Data

Aug. 25, 2000 (DK) .............................. 2000 01258

(51) Int. Cl.
*A61B 1/00* (2006.01)
*A61B 1/04* (2006.01)

(52) U.S. Cl. ................. 600/117; 600/103; 600/129
(58) Field of Classification Search ................. 600/103, 600/111, 117–118, 129, 166, 170, 173, 407, 600/476; 356/241.1–241.5

See application file for complete search history.

(56) References Cited

U.S. PATENT DOCUMENTS

| 4,089,608 A | 5/1978 | Hoadley ..................... 356/156 |
| 4,185,918 A | 1/1980 | DiMatteo et al. ............ 356/375 |
| 4,575,805 A | 3/1986 | Moermann et al. .......... 364/474 |
| 4,705,401 A | 11/1987 | Addleman et al. .......... 356/376 |
| 4,737,032 A | 4/1988 | Addleman et al. .......... 356/376 |
| 4,871,502 A | 10/1989 | LeBisch et al. |
| 4,984,277 A | 1/1991 | Bisgaard et al. |
| 5,006,055 A | 4/1991 | Lebisch et al. |
| 5,008,058 A | 4/1991 | Henneberger et al. |

(Continued)

FOREIGN PATENT DOCUMENTS

AU 762679 1/2001

(Continued)

*Primary Examiner*—John P Leubecker
*Assistant Examiner*—Philip R Smith
(74) *Attorney, Agent, or Firm*—Jacobson Holman PLLC

(57) ABSTRACT

A scanner for three-dimensional scanning of interior surfaces or cavities of limited dimensions or with restricted accessibility. The scanner includes a probe having an axis and at least one light source and one camera adapted to perform a scan 360° around the axis of the probe. High precision three-dimensional replicas of real objects may be created using 3-D scan data obtainable with the scanner.

42 Claims, 13 Drawing Sheets

U.S. PATENT DOCUMENTS

| | | | | |
|---|---|---|---|---|
| 5,027,281 | A | 6/1991 | Rekow et al. | 364/474.24 |
| 5,056,204 | A | 10/1991 | Bartschi | 29/169.5 |
| 5,121,333 | A | 6/1992 | Riley et al. | |
| 5,121,334 | A | 6/1992 | Riley et al. | |
| 5,128,870 | A | 7/1992 | Erdman et al. | 364/474.05 |
| 5,172,685 | A | 12/1992 | Nudelman | 128/6 |
| 5,184,306 | A | 2/1993 | Erdman et al. | 364/474.05 |
| 5,257,203 | A | 10/1993 | Riley et al. | |
| 5,276,407 | A * | 1/1994 | Mead et al. | 330/308 |
| 5,381,786 | A * | 1/1995 | Spears | 600/117 |
| 5,432,543 | A * | 7/1995 | Hasegawa et al. | 348/45 |
| 5,487,012 | A * | 1/1996 | Topholm et al. | 700/163 |
| 5,501,096 | A | 3/1996 | Stettner et al. | 73/1 J |
| 5,506,683 | A | 4/1996 | Yang et al. | 356/376 |
| 5,547,455 | A * | 8/1996 | McKenna et al. | 600/113 |
| 5,549,476 | A | 8/1996 | Stern | 433/223 |
| 5,552,992 | A | 9/1996 | Hunter | 364/468.25 |
| 5,561,526 | A | 10/1996 | Huber et al. | 356/376 |
| 5,661,667 | A | 8/1997 | Rueb et al. | 364/525 |
| 5,717,455 | A * | 2/1998 | Kamewada | 348/85 |
| 5,741,215 | A | 4/1998 | D'Urso | 600/407 |
| 5,753,931 | A | 5/1998 | Borchers et al. | 250/559.22 |
| 5,784,098 | A | 7/1998 | Shoji et al. | 348/45 |
| 5,831,719 | A | 11/1998 | Berg et al. | 356/5.13 |
| 5,864,640 | A | 1/1999 | Miramonti et al. | 382/312 |
| 5,870,220 | A | 2/1999 | Migdal et al. | 359/216 |
| 5,889,874 | A | 3/1999 | Schmitt et al. | |
| 5,895,927 | A | 4/1999 | Brown | 250/559.19 |
| 5,936,628 | A | 8/1999 | Kitamura et al. | 345/420 |
| 5,940,170 | A | 8/1999 | Berg et al. | 356/5.1 |
| 5,978,092 | A | 11/1999 | Brown | 356/376 |
| 5,991,437 | A | 11/1999 | Migdal et al. | 382/154 |
| 6,035,229 | A * | 3/2000 | Silverstein et al. | 600/473 |
| 6,044,170 | A | 3/2000 | Migdal et al. | 382/154 |
| 6,081,273 | A | 6/2000 | Weng et al. | 345/425 |
| 6,248,074 | B1 * | 6/2001 | Ohno et al. | 600/463 |
| 6,263,234 | B1 | 7/2001 | Engelhardt et al. | 600/476 |
| 6,293,911 | B1 * | 9/2001 | Imaizumi et al. | 600/160 |
| 6,320,331 | B1 * | 11/2001 | Iida et al. | 315/293 |
| 6,377,865 | B1 | 4/2002 | Edelsbrunner et al. | |
| 6,533,062 | B1 | 3/2003 | Widmer et al. | |
| 6,545,676 | B1 | 4/2003 | Ryan et al. | |
| 6,629,065 | B1 | 9/2003 | Gadh et al. | |
| 6,725,184 | B1 | 4/2004 | Gadh et al. | |
| 6,751,494 | B2 * | 6/2004 | Collier et al. | 600/407 |
| 6,920,414 | B2 * | 7/2005 | Tøpholm | 703/1 |
| 6,928,396 | B2 | 8/2005 | Thackston | |
| 7,050,876 | B1 | 5/2006 | Fu et al. | |
| 7,162,323 | B2 | 1/2007 | Brumback et al. | |
| 2001/0031912 | A1 * | 10/2001 | Adler | 600/109 |
| 2003/0074174 | A1 | 4/2003 | Fu et al. | |
| 2003/0152242 | A1 | 8/2003 | Marxen et al. | |

FOREIGN PATENT DOCUMENTS

| | | |
|---|---|---|
| DE | 41 02 614 | 1/1991 |
| DE | 198 03 679 | 8/1999 |
| EP | 0 352 952 | 1/1990 |
| EP | 0 233 920 | 1/1991 |
| EP | 0 490 848 A2 | 6/1992 |
| EP | 0 516 808 | 1/1996 |
| EP | 1 062 916 | 12/2000 |
| GB | 2 104 652 | 3/1983 |
| JP | 11-337845 | 12/1992 |
| JP | 9103000 | 4/1997 |
| WO | 91/13586 | 9/1991 |
| WO | WO 92/11737 | 7/1992 |
| WO | 96/10205 | 4/1996 |
| WO | 97/32182 | 9/1997 |
| WO | 98/59300 | 12/1998 |
| WO | 99/28704 | 6/1999 |
| WO | 00/04506 | 1/2000 |
| WO | 00/04508 | 1/2000 |
| WO | WO 00/07501 | 2/2000 |
| WO | 00/34739 | 6/2000 |
| WO | WO 01/05207 A2 | 1/2001 |
| WO | 01/22030 | 3/2001 |

* cited by examiner

METHOD AND APPARATUS FOR THREE-DIMENSIONAL OPTICAL SCANNING OF INTERIOR SURFACES

This is a nationalization of PCT/DK01/00561 filed Aug. 24, 2001 and published in English.

TECHNICAL FIELD

The invention relates to the creation of high precision three-dimensional replicas of real objects. The invention specifically concerns the three-dimensional scanning of interior surfaces or cavities of limited dimensions or with restricted accessibility. Furthermore, the invention relates to a specific embodiment for scanning the human ear and ear canal.

PRIOR ART

Systems for three-dimensional optical scanning are well known in the prior art. They typically comprise one or more light sources projecting a structured light pattern on the object to be scanned, one or more cameras and data processing equipment to convert the recorded image co-ordinates to three dimensional co-ordinates using state of the art software. Usually, only a part of the object is scanned in a single scan. To create a full scan the object, camera and light source need to be move relative to each other.

Precision is of utmost importance in many applications, e.g. when the scan data is used to model an object, which must fit precisely into another part. Such applications are e.g. devices for the ear canal such as hearing aids, dental implants and other prostheses for the body. For hearing aid shells sub-millimeter precision is required or the shell will cause irritation, acoustic feedback and possibly infection to the epidermis of the ear canal. For dental implants the precision requirement is even greater, since a human being can detect differences less than $\frac{1}{10}$ of a millimeter when biting. Therefore systematic or random errors in the calibration and/or performance of scanners for these uses can be fatal. This has hitherto limited the use of scanning in the modelling of such implants and shells.

WO 96/10204 (Fright et al.) discloses a handheld 3-D scanner, which uses a position sensor to determine the relative position of the scanner with respect to the object to be scanned. The disclosed scanner is not adapted to scan interior surfaces due to its size and due to the fact that the light sources point towards the centre of in which the object to be scanned must be placed. This scanner thus suffers from the same occlusion effects as non-portable scanners. The patent application is the basis for the Polhemus FastTrack handheld scanner.

U.S. Pat. No. 6,263,234 (Leica Microsystems Heidelberg GmbH) discloses a confocal surface-measuring device, which is adapted to emit a ray of light and partly move this ray in relation to the axis of the device to perform a scan of an area below the device. The invention dos not disclose how the light reflected from the object is directed to the detector, which makes it very doubtful whether the construction is able to work in practice. However the scanner only rotates the light deflecting means and not the construction related to the detector, which only makes it able to scan a very limited part of the circumference.

U.S. Pat. No. 5,895,927 (USA Secretary of the Air Force) discloses a non-contact interior cross-section profiler for measuring internal dimensions of pipes, tubes etc. The profiler generates a disc of light using a cone shaped mirror which is reflected from the interior surface of the pipes, tubes etc. to a camera. It is however doubtful whether the profiler can measure the dimensions precisely, since small errors in the orientation of the profiler along the axis of the pipe or tube will cause the disc to be distorted. The profiler is only meant to measure internal dimensions and not to produce 3-D real world co-ordinates.

U.S. Pat. No. 5,784,098 (Olympus Optical Co., Ltd.) discloses an endoscope which is capable of performing 3D scanning of small areas in the interior of a human being. The scanner works by projecting a pattern consisting of several sheets of light from the tip of the endoscope onto the surface in front of the tip. 2-D images are taken by a camera connected via light guides to the tip of the endoscope. Due to this construction, the angle at which light is reflected from the surface towards the camera is very small and not optimal for precision scanning. Furthermore, the scanner is only adapted to map small areas. Additionally the design is very likely to give very distorted images, which makes high precision scanning infeasible.

WO 01/22030 (Mycrona Gesellschaft für Innovative Messtechnik GmbH) discloses a device for measurement of poorly accessible hollows such as the inside of a bore. The device is capable of measuring the internal diameter of the hollow. However the scanner is only able of perform scans at maximal 180° of the circumference, since it only applies one or two static coplanar mirrors.

U.S. Pat. No. 5,056,204 (Ascom Audiosys AG) concerns a method for milling of hearing aids whereby the internal contours of the ear canal are allegedly recorded by a laser apparatus located outside the ear of the patient. The disclosure contains no means to direct the laser light into the ear canal. Due to occlusion effects only part of the ear canal can be scanned according to the disclosed method. Furthermore, the disclosure fails to take regard to the fact that the individual is likely to move while the images are recorded.

WO 00/34739 (Fagan et al.) concerns a method for manufacturing hearing aid shells involving the use of a specially adapted ultrasonic scanner head to safely measure the contours of the ear canal without contact with the surface being measured. The recording of the data in the ear canal is made possible by filling the canal with a liquid and inserting the ultrasonic scanner. The scan data are processed by a computer and the data are used with a rapid prototyping set-up such as stereo lithography, selective laser sintering, laminate object modelling, inkjet modelling, fused depositing modelling, 3DP or any other system that produces real models from computer mathematical models to manufacture the hearing aid shell. One disadvantage of the system is the need for filling the patient's ear completely with water. This can be extremely annoying to patients and they may experience symptoms of nausea during and after such treatment. Furthermore it is doubtful whether it is really possible to determine the three dimensional co-ordinates of the surface of the ear canal with the required precision using an ultra sonic scanner. An ultrasonic sound signal emitted does not travel in just one direction in the liquid in the ear canal. As the ultrasonic waves are reflected by the surface of the ear canal they travel in many different directions. Thus the transducers of the ultrasonic scanner will detect a number of signals of varying size with different delays after the emission of one sound signal. It must be extremely difficult for the underlying software to determine which of the signals to use in the determination of the co-ordinates. The disclosure provides no information on how to perform this operation.

EP 0 516 808 (Topholm & Westermann Aps) concerns a method for computer assisted manufacture of otoplastic individually fitted to the contours of the ear canal.

According to the described method a digital representation of the internal contours of the ear canal is used for milling or 3D printing of a hearing aid shell. A computer is used to optimise the location of the components of the hearing aid and the thickness of the walls of the shell. The disclosure does not suggest the solution of scanning the internal contours of the ear canal using an optical scanner.

SUMMARY OF THE INVENTION

According to a first aspect the invention relates to a scanner for three-dimensional scanning of interior surfaces comprising

- at least one light source adapted to create and project structured light producing a pattern on the interior surface of an object,
- at least one camera, adapted to record 2-D images of the pattern,
- data processing means adapted to convert 2-D image information into 3-D real world co-ordinates,
- the point of emission of light as well as the point of accumulation of reflected light for the camera being located on a probe having an axis,
- the at least one light source and the at least one camera being adapted to perform a scan 360° around the axis, and
- the probe being adapted to be entered into a cavity.

The probe of the scanner may be either rigid of flexible

Compared to prior art scanners this scanner has the advantage that it is able to cover the whole circumference without moving the scanner thus being able to scan the whole inner surface of an object. With this layout it is possible to scan interior surfaces such as the ear canal, tubes, pipes and bores with non-contact scanning and obtain high precision scan data of the whole interior surface of the object.

Furthermore, the dimensions of the scanner can be very small thus allowing scanning and 3D mapping of interior surfaces with small cross section, which are inaccessible to prior art scanners.

According to an especially preferred embodiment the scanner is equipped with a position sensor, which allows the relative position and orientation of the scanner and the object to be determined for successive scans. This greatly facilitates the combination of data from successive scans and makes it possible to combine these with much higher precision irrespective of the position and orientation of the scanner during scanning.

According to another aspect the invention relates to the use of a scanner according to the invention. Among the preferred uses are scanning of body cavities, scanning of industrial objects, scanning in connection with archaeology and scanning in connection with industrial design.

The compact layout of the scanner allows for easy scanning of interior surfaces of objects of extremely small size. The ease of operation of the scanners according to the invention means that practitioners without experience in scanning can easily perform the scanning operations, which is required especially in the case of scanning of body cavities and scanning for archaeological purposes.

According to a further aspect the invention relates to a method for scanning interior surfaces comprising the steps of
i) entering a probe shaped scanner having an axis into a cavity,
ii) creating and projecting structured light from a first point on the probe producing a pattern on an interior surface of an object, and at a second point of the probe, recording 2D images of the pattern reflected from the interior surface, thereby performing a scan 360° around the axis of the probe,
iii) determining 2D co-ordinates of the images of the pattern,
iv) combining a series of images to obtain 3D real world co-ordinates of the interior surface.

The method allows for easy scanning of interior surfaces of objects which cannot be scanned with high precision using prior art scanning methods.

Preferably the method is carried out with a scanner according to the invention.

According to a preferred embodiment the method for scanning further comprises calibration of the scanner by:
i) scanning a three dimensional calibration object having at least one plane of symmetry and whereby at least part of at least one 3D object feature curve of each symmetric part is a continuous curve,
ii) determining image feature co-ordinates being representations of at least one pair of 3D object feature curves for each of a discrete number of values of an angle or rotation and/or translation, a pair consisting of one 3D object feature curve in each symmetric part of the calibration object,
iii) changing the calibration parameters to fit the calibration object.

According to a still further aspect the invention relates to a method for 3D modelling and production comprising obtaining 3D real world co-ordinates of an interior surface of a cavity provided using the method according to the invention, and creating a piece adapted to fit into the cavity.

Thereby, the steps for manufacturing the piece are reduced to the absolute minimum and an especially perfect fit of the piece can be obtained. The interior surface may be scanned a number of times, such as under different conditions affecting the geometry of the interior surface. Thereby the variations in the dimensions of the interior surface can be recorded. This is very cumbersome using the prior art techniques.

Once the data are recorded the piece may be manufactured using any automatic manufacturing technique such as milling. More preferably the modelling technique comprises 3-dimensional printing, stereo lithography, selective laser sintering, laminated object modelling, inkjet modelling, fused deposition modelling, nano-printing. A common feature of these techniques is that only the required amount of material is used and that it is easier to produce complex models such as devices for the ear and/or ear canal and/or dental implants.

The devices for the ear may comprise a hearing aid, a mobile phone, a loud speaker, a microphone, communication devices, a tinnitus masker or a tinnitus masking device such as the ones described in U.S. Pat. No. 5,325,872 and WO 91/17638. FIG. 13 shows a scan of the interior surface of an ear and an ear canal 1301.

DETAILED DESCRIPTION OF THE INVENTION

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 5:
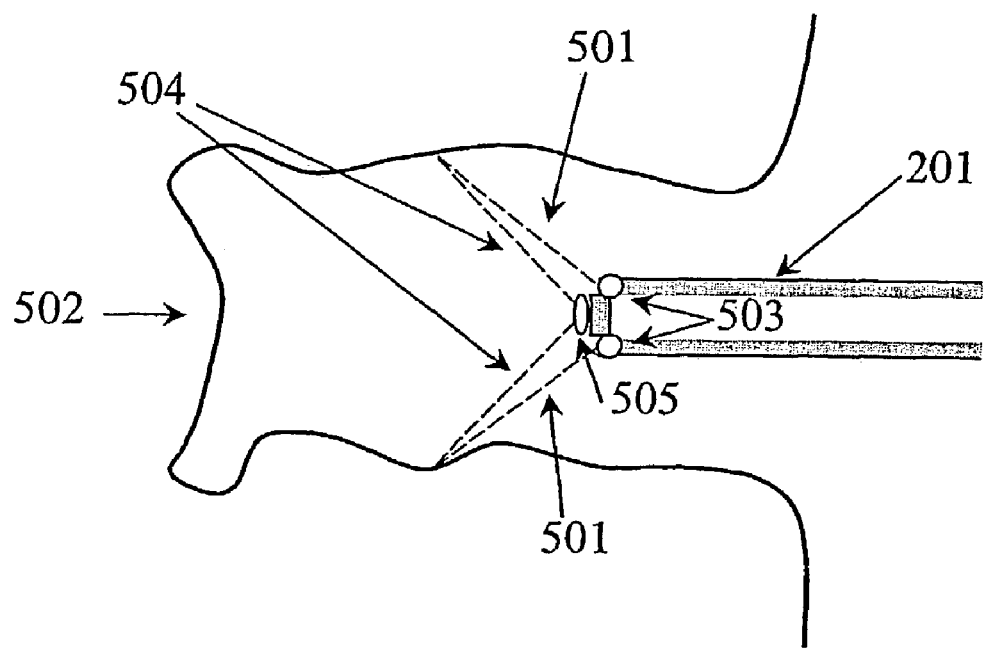
FIG. 5 shows how a structured light pattern is projected onto the interior surface. In this case the pattern is a single cone. This pattern is then reflected from the surface into the camera.

FIG. 1 to FIG. 4 illustrate two preferred embodiments of the invention. The first part 101 of the scanner is the probe, which is inserted into the cavity. The second part 102 is a handle. The scanner in FIG. 1 and FIG. 2 comprises a cover 103, a scan button 104, a disposable cover 105, light guides 201, a light source 202, a position sensor 203, optics and mirrors and/or prisms 204, a camera 205 and a protector/collision detector 206. A rotating mirror and/or prism with a micro motor 301 is also added to the component list in the embodiment shown in FIG. 3 and FIG. 4. As illustrated in FIG. 5, the scanner works by projecting a structured light pattern 501 onto the interior surface of the object 502. The camera 503 acquires images of the reflection 504 of the light pattern from the surface. By locating the light pattern in the images, the corresponding 3D surface positions can be reconstructed applying well-known projective geometry. The scanner only scans limited parts of the surface at each position and usually it has to be moved around handheld or automatically to scan the full interior surface.

Light Pattern Generation

The light is generated by one or more light sources such as lasers, variable output-powered laser, laser emitting diodes (LED), halogen spots or other spotlights and travels through the light guides such as optical fibres. In some applications it might be relevant to use monochromatic, coherent or polarised light. At the end of the light guides optics and mirrors and/or prisms may create the desired pattern. Examples of optics are filters, lenses or prisms. An alternative to the use of light guides is to place the light source near the tip of the scanner. Note that the projection of light, even lasers, onto the surface does not damage the surface.

The light sources for some applications preferably are as small as possible to minimise the dimensions of the scanner. It is thus contemplated that the light source may have a cross section perpendicular to the direction of emitted light of less than 5 mm, preferably less than 4 mm, for example less than 3 mm, such as less than 2 mm, for example less than 1 mm, such as less than 0.5 mm, for example less than 0.25 mm.

The scanner may work with only one light source, but for many purposes it is advantageous to have several such as at least 2 light sources, such as at least 3 light sources, for example at least 4 light sources, such as at least 5 light sources, such as at least 6 light sources, for example at least 7 light sources, such as at least 8 light sources, for example at least 10 light sources, such as at least 12 light sources, for example at least 16 light sources, such as at least 20 light sources.

Depending on the desired pattern one, two, three or more optics and one, two, three, four or more mirror and/or prisms are required. The structured light pattern may be a number of rays forming a grid of spots on the surface consisting of one, two, three, four or more rows of points, one, two, three or more cones of light forming contours on the surface, one, two, three of more planes of light forming contours on the surface, one, two, three of more thick planes of light forming thick contours on the surface, a number of rectangular shaped rays forming a distorted checker board pattern on the surface or more complex shapes.

Thus, when projecting a pattern of rays, pattern may comprise at least 10 rays, such as at least 25 rays, for example at least 100 rays, such as at least 1000 rays, for example at least 10,000 rays, such as at least 100,000 rays, for example at least 1,000,000 rays.

Figure 6:
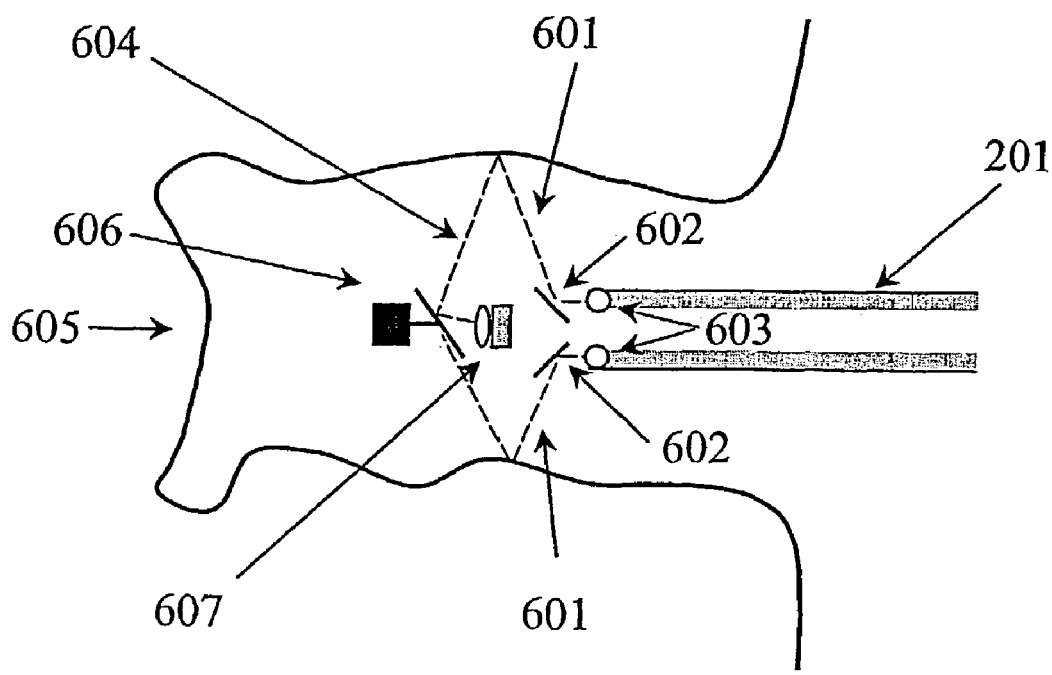
FIG. 6 illustrates an example of the use of mirrors and/or prisms. A structured light pattern is reflected in a mirror before being projected onto the interior surface. In this case the pattern is a single cone. This pattern is then reflected from the surface into a mirror that reflects the pattern into the camera.

FIG. 5 illustrates how a single light cone 501 is projected onto the object surface 502 using optics 503. FIG. 6 shows how the emission angle of the light cone can be increased significantly by reflecting the emitted light 601 into a cone mirror and/or prism 602 after the optics 603. Any type of mirrors such as coplanar mirrors and cone mirrors can be used to reflect the light. Applying mirrors and/or prisms make it possible to change the emission direction invariant of the orientation of the light guides. The light pattern can also be moved over the surface without moving the actual scanner by rotating and/or tilting the mirrors and/or prisms. The rotation and/or tilting of the mirrors and/or prisms may be carried out by a motor.

Preferably the location of the point of emission of light and the point of recording reflected light as well as the angle of emission and recording with respect to the axis of the probe are chosen to give an angle between incident light on the object and light reflected from the object of approximately 20-30°. An example of this embodiment is illustrated in FIG. 6.

Occlusion effects represent a problem for some types of scanning of interior surfaces. Some of these can be overcome by selecting a direction of emission and recording of light with respect to the axis of the scanner, which ensures that light is projected on and recorded from all parts of the interior surfaces. One embodiment of the scanner is designed, wherein the location of the point of emission of light and the point of recording reflected light as well as the angle of emission and recording with respect to the axis of the probe are chosen to give a scan of the surface lying ahead of the end of the probe. An example of such a scanner is shown in FIG.

Figure 14:
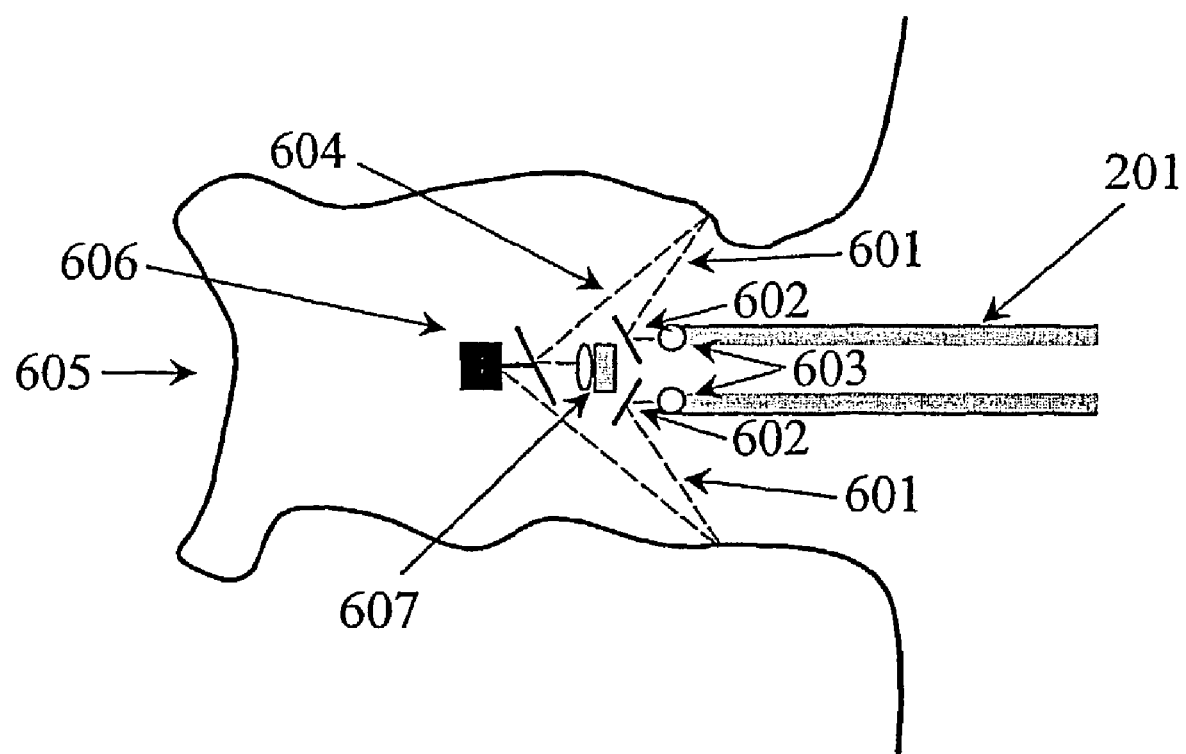
FIG. 14 illustrates an embodiment of the scanner being able to scan the surface lying behind the end of the probe.

5. Alternatively the location of the point of emission of light and the point of recording reflected light as well as the angle of emission and recording with respect to the axis of the probe may be chosen to give a scan of the surface lying approximately around the end of the probe. An example of this is shown in FIG. 6. Alternatively, the location of the point of emission of light and the point of recording reflected light as well as the angle of emission and recording with respect to the axis of the probe may be chosen to give a scan of the surface lying behind the end of the probe. FIG. 14 illustrates an example of such a scanner. These alternative embodiments may be obtained with one scanner by tilting mirrors and/or prisms.

Light Source Intensity Adjustment

The light source intensities are preferably varied depending on the surface and colour of the object to be scanned. Preferably the intensity should be determined automatically using automatic light source intensity calibration.

The intensity calibration may be performed by inserting the scanner into the object and calculate a number of histograms from the acquired images. First a histogram is calculated with the light source turned off. A second histogram is the calculated when the light source is turned on with an arbitrary intensity. The first histogram is then subtracted from the second to remove the background intensity. The intensity is then adjusted until the requested quantile corresponds to a predefined intensity. The background could also be removed by subtracting the image corresponding to the light source turned off from the image with light. The histogram used to determine the intensity could then be calculated from this difference image.

Image Acquisition

The images are acquired by the one or more cameras. Preferably the cameras comprise a lens and a sensor array such as a CCD or CMOS chip. Usually the camera also comprises a filter placed in front of the sensor array. The effect of the filter is that only light with approximately the desired wavelength passes the filter. This makes it feasible to separate different light sources in the scanner and remove most of the background light. Alternatively, the camera may be colour sensitive.

The scanner may comprise just one camera or comprise several such as at least 2 cameras, such as at least 3 cameras, for example at least 4 cameras, such as at least 6 cameras, for example at least 7 cameras, such as at least 8 cameras, for example at least 10 cameras, such as at least 12 cameras, for example at least 16 cameras, such as at least 20 cameras.

Figure 11:
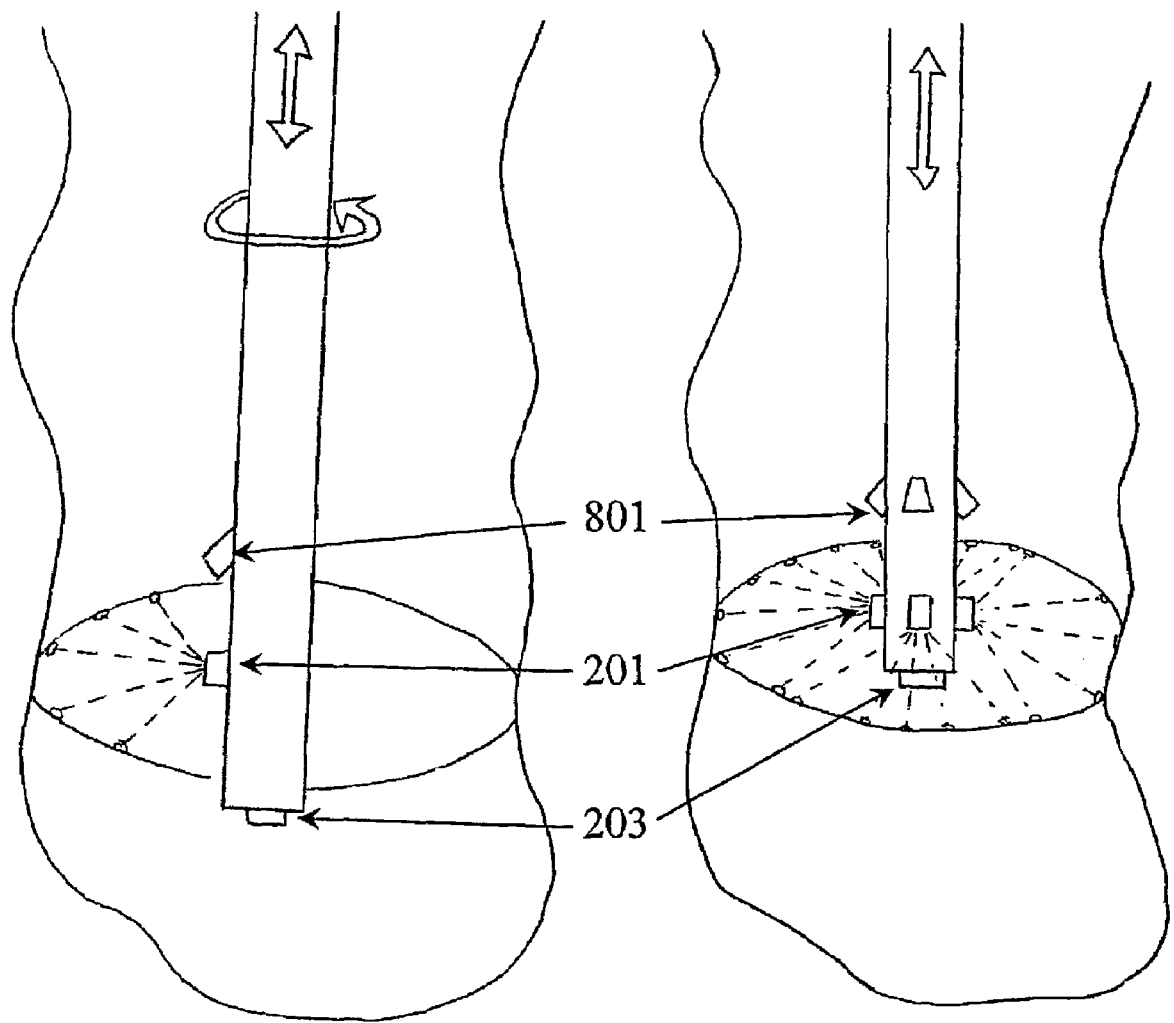
FIG. 11 shows a schematic sketch of a scanner according to the invention adapted for scanning of the ear and ear canal.
Figure 12:
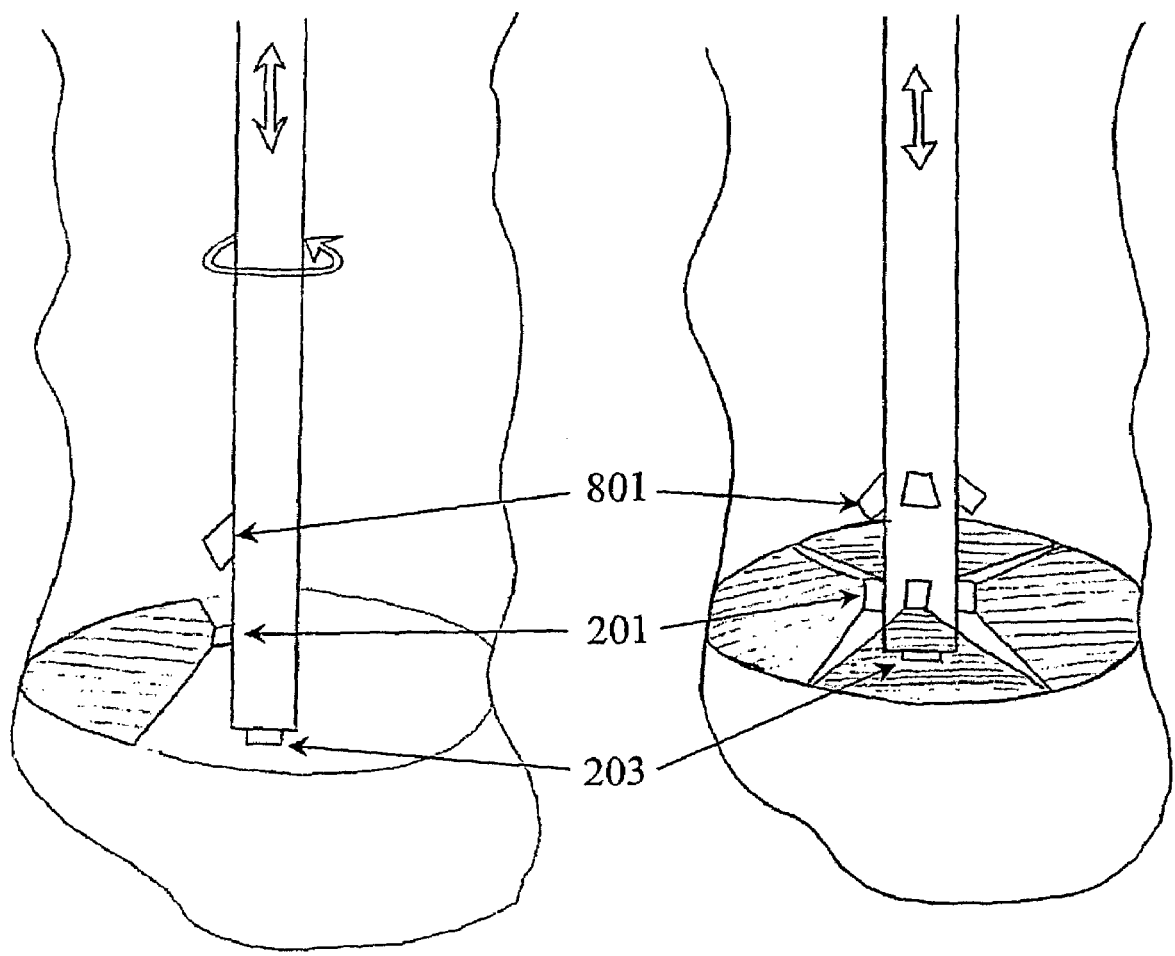
FIG. 12 shows a schematic sketch of another embodiment of the scanner for the ear and ear canal.

Preferably the cameras are arranged such that reflected light is recorded from different directions covering the 360° around the probe (FIGS. 11 and 12, right side).

Preferably the camera part of the scanner is as small as possible. The size of cameras is reduced almost every year, and it is estimated that the lower limit for camera size and pixel size have not been reached at all yet. Irrespective of the future development within this area, camera smaller than the cameras presently available will be suitable for use in the present invention. Therefore the light detecting component of the camera may have a cross section in a direction perpendicular to the direction of incident light of less than 10 mm, such as less than 9 mm, for example less than 8 mm, such as less than 7 mm, for example less than 6 mm, such as less than 5 mm, for example less than 4 mm, such as less than 3 mm, for example less than 1 mm, such as less than 0.5 mm, for example less than 0.25mm, such as less than 0.1 mm, for example less than 0.01 mm.

The number of pixels of the camera is a question of the size of the camera (depending on the size of the pixels), the computing power used for processing the results of the scans and the cost of the camera. No upper limit for the number of pixels can be set, since precision is increased whenever the number of pixels is increased. Accordingly, the camera may comprise an array of at least 125*125 pixels, more preferably at least 250*250 pixels, more preferably more than 500*500 pixels, more preferably more than 1000*1000 pixels, such as more than 2000*2000 pixels, for example more than 4000*4000 pixels, such as more than 8000*8000 pixels, for example more than 10,000*10,000 pixels, such as more than 25,000*25,000 pixels, for example more than 50,000*50,000 pixels, such as more than 100,000*100,000 pixels, for example more than 250,000*250,000 pixels, such as more than 500,000*500,000 pixels, for example more than 1,000,000*1,000,000 pixels. Similarly, the pixel size may be the smallest available on the market, for example wherein a cross section of a pixel is less than 100 µm, such as less than 50 µm, for example less than 25 µm, such as less than 20 µm, for example less than 15 µm, such as less than 10 µm, for example less than 7.5 µm, such as less than 5 µm, for example less than 2.5 µm, such as less than 2 µm, for example less than 1.5 µm, such as less than 1 µm, for example less than 0.5µ, such as less than 0.25 µm, for example less than 0.1 µm, such as less than 0.01 µm.

The light pattern may be reflected from the surface directly into the camera or into one or more light reflecting means such as mirrors or prisms before ending up in the camera. In the embodiment of the scanner in FIG. 1 no mirrors are applied, since the scanner only needs to "look" forward with respect to the camera, i.e. the direction of the view is always parallel with the optical axis of the camera. FIG. 5 illustrates the simple emission of the light pattern 501 and its reflections 504 from the object surface 502 into the camera 505 without the use of mirrors. FIG. 5 is a simplified illustration of the principle used in the scanner in FIG. 1.

Applying one or more mirrors and/or prisms for reflecting the light into the camera gives full freedom to select the direction of the view invariant of the orientation of the camera. FIG. 6 illustrates how the emitted light pattern 601 is reflected using a cone mirror and/or prism 602 before it hits the object surface 605. The reflected light 604 is likewise reflected into a mirror and/or prism 606 before entering the camera 607. FIG. 6 is a simplified illustration of the principle used in the scanner in FIG. 3. Static mirrors such as coplanar or cone mirrors can be applied directly in the invention. Static mirrors have the advantage of being simple and mechanically stable.

Figure 3:
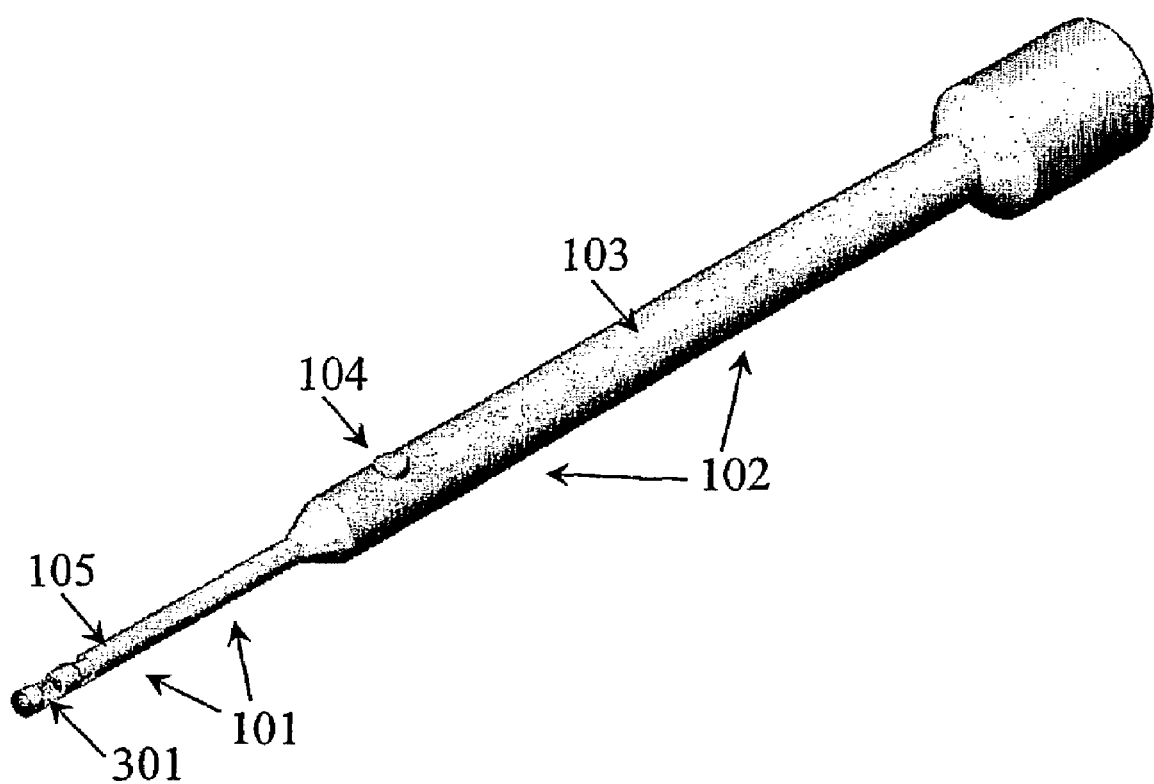
FIG. 3 illustrates another embodiment of the interior surface scanner with a mirror in front of the camera.
Figure 4:
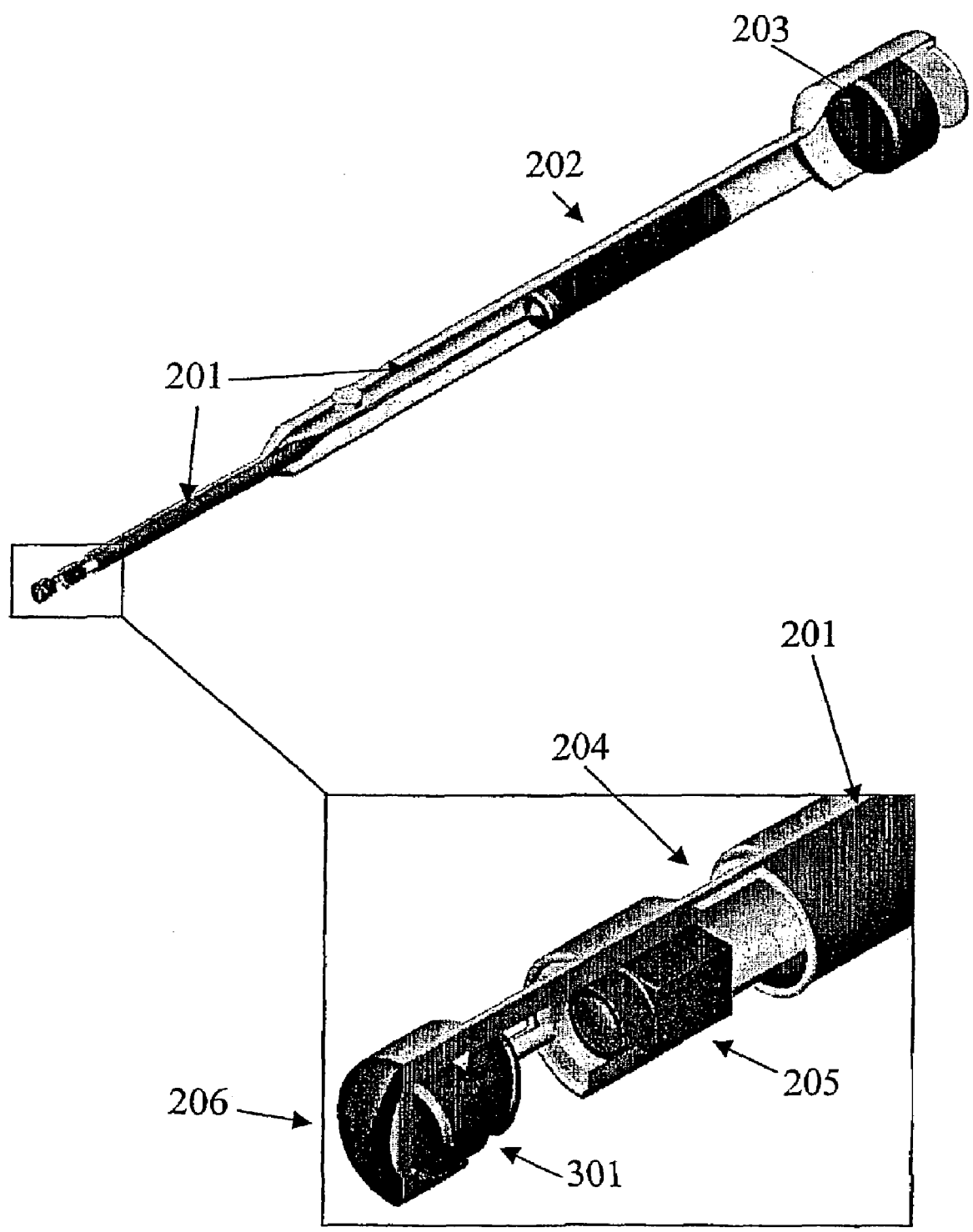
FIG. 4 shows a cross section of another embodiment of the interior surface scanner with a mirror in front of the camera.

In the embodiment of the scanner shown in FIG. 3 the mirror and/or prism in front of the camera is coplanar, circular and able to rotate. The advantage of a rotating mirror and/or prism compared to a static mirror and/or prism, such as a cone mirror and/or prism, is that the image resolution and the field of view of the camera are significantly increased. Indeed resolution and field of view are seriously limited due to the small dimensions of the scanner, which directly affect the accuracy and flexibility. Tilting the mirror and/or prism further increases the accuracy and flexibility. In practice, the same mirror and/or prism can be used to generate the light pattern and reflecting the light into the camera. However, applying different mirrors and/or prisms for light and cameras, as presented in FIG. 3, increase the flexibility of the scanner especially with respect to direction of view, depth of field and point reconstruction quality.

Figure 7:
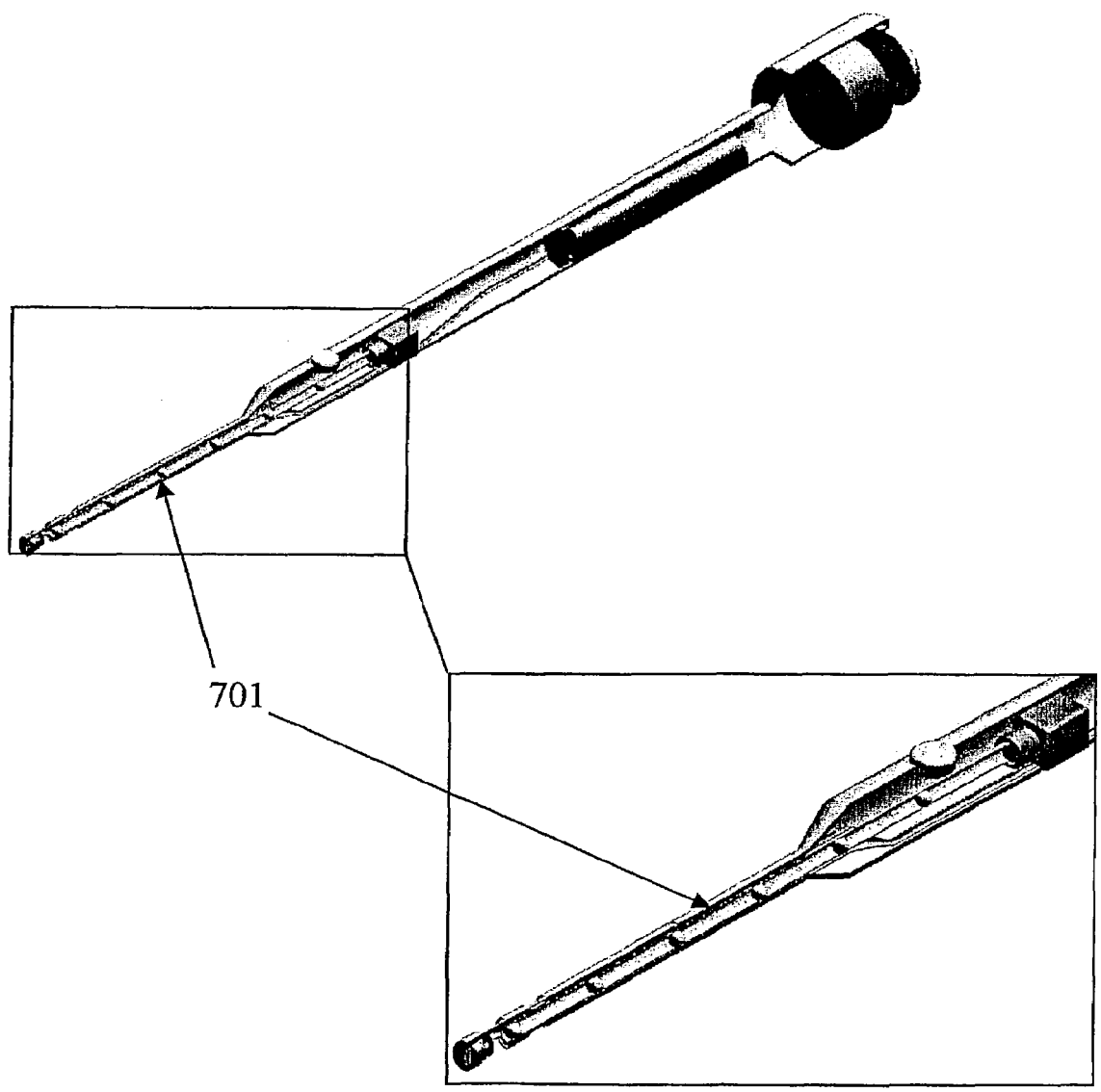
FIG. 7 shows a cross section of a model of the interior surface scanner according to the invention. Note that the camera has been moved out of the probe and a lens system is used to guide the image to the camera.
Figure 8:
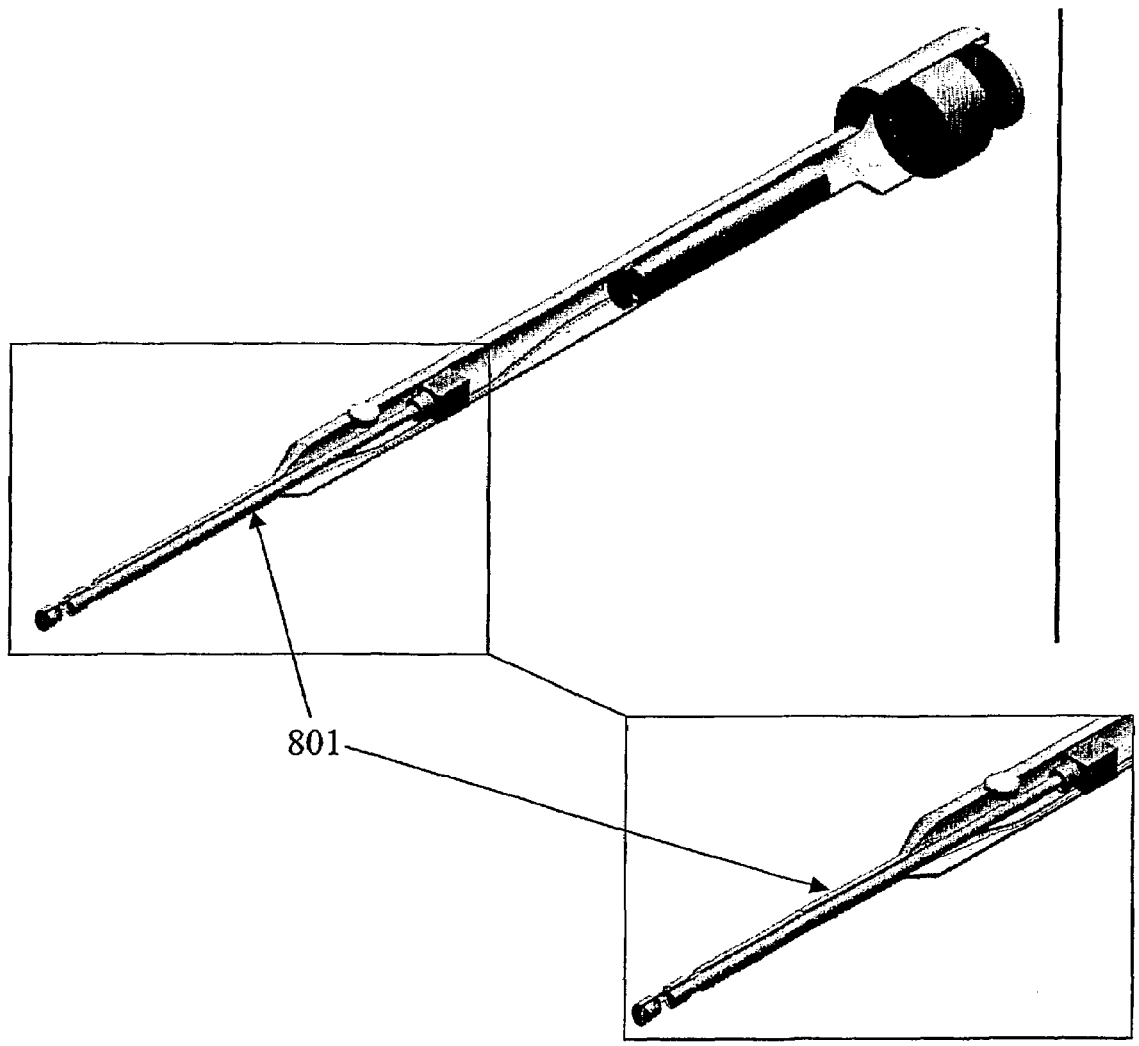
FIG. 8 shows a cross section of a model of the interior surface scanner according to the invention. Note that the camera has been moved out of the probe and optical fibres are used to guide the image to the camera.

In the case of very small dimensions of the cavity and/or high requirements for accuracy it is infeasible to place the camera on the head of the scanner. The problem is solved by moving the cameras out of the probe. The image/light is then directed into the cameras by the use of light guides such as a lens system or optical fibres. An embodiment of the invention where a lens system 701 and optical fibres 801 are used as light guides are illustrated in FIG. 7 and FIG. 8, respectively. The lens system might be similar to the lens systems used in periscopes and endoscopes. At the moment the lens system is superior to optical fibres with respect to smallest dimensions and image quality. The disadvantage of the lens system is that it requires the probe be rigid, whereas the optical fibres are fully flexible, i.e. the probe can be flexible.

Position Sensing

The objective of the position sensor is to determine the relative position and orientation of the probe head with respect to the object to be scanned. Knowing this position is extremely advantageous in combining the individual scans when the scanner or object is moved. Errors in the position measures will directly affect the quality of the scan. In the case of non-fixed objects such as the ear canal of humans are scanned, it is extremely advantageous to measure the position with respect to the object, e.g. the ear canal, and not to a fixed coordinate system, since the object might move during the scanning.

Recall that the position sensor is only required to combine the individual scans. The position sensor can be rendered superfluous by a registration of the individual scans. The output of the registration is the relative position of the scans. Knowing the relative positions of the scans make it straightforward to combine the scans. For the registration to be successful the interior surface needs to contain a proper number of distinct features, which is not always the case.

Figure 9:
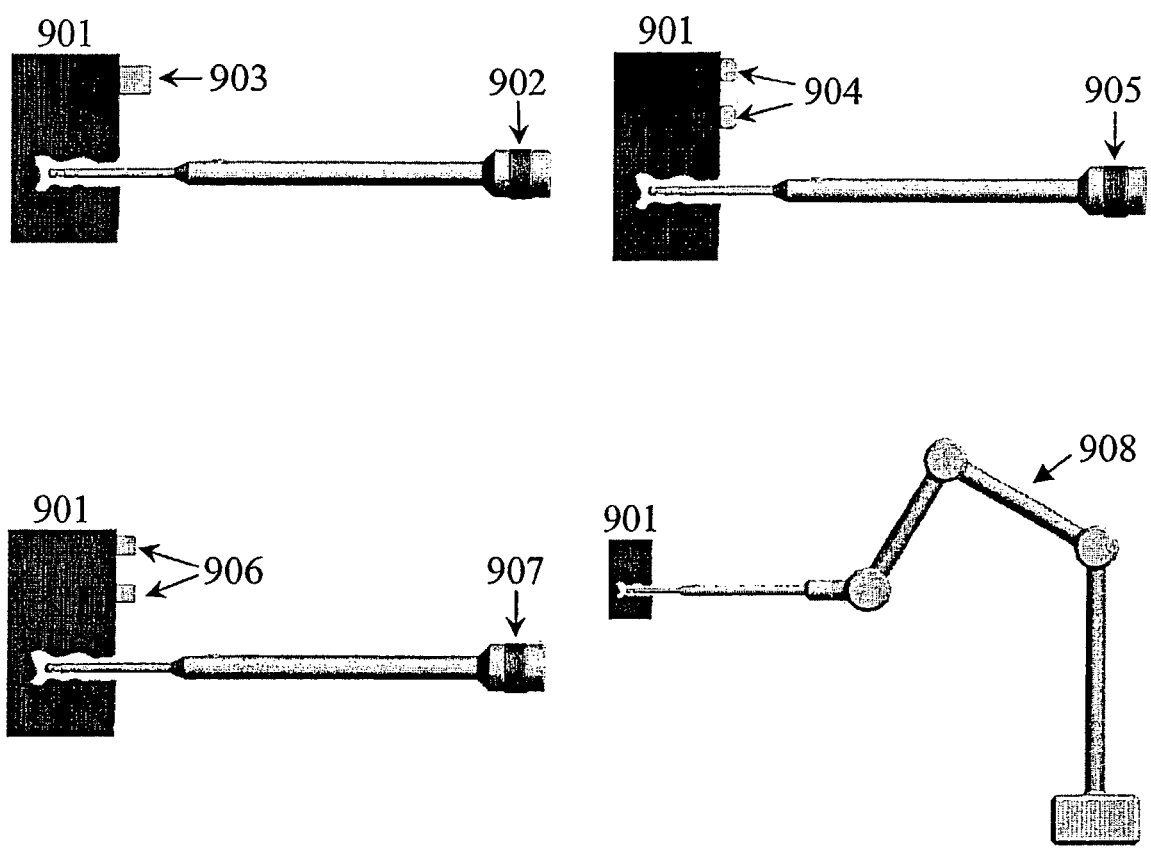
FIG. 9 illustrates different positions sensors, which can be applied within the invention.

Preferably the position sensor should be a magnetic sensor as shown in FIG. 9, where the receiver 902 usually is in the scanner and the transmitter 903 is secured to the object 901, e.g. the head of a human. Magnetic sensors have the advantage of not suffering for occlusion problems. Alternative sensors might be optical or sonic sensors. FIG. 9 illustrates an optical sensor where markers 904 are placed on the object and a sensor 905 on the scanner. Likewise FIG. 9 illustrates a sonic sensor, where an emitter 906 is placed on the object and a detector 907 is placed on the scanner. Both optical and sonic sensors suffer from occlusion problems, but their cost is often lower and the precision superior to those of magnetic sensors. In the case of a fixed object or an object, which can be fixed, a mechanical position sensor becomes attractive. As illustrated in FIG. 9 these sensors usually consist of a number of joints 908 connected by encoders. Many mechanical sensors are highly accurate, but they tend to be bulky or cumbersome to use.

In general, the position needs to be determined with respect to the head of the scanner. More precisely, the position of the focal point of the camera has to be determined when the camera is placed on the probe head. In the case where light guides are used in front of the camera, the position should correspond to the tip of the guides. With a rigid design of the scanner cover as in FIG. 1 to FIG. 4 the position sensor can be placed anywhere on the scanner, since the relative distance between the scan head and the position sensor is constant. With a flexible design of the probe the position sensor needs to be placed on the scan head, e.g. at the front as on the scanner in FIG. 11 and FIG. 12.

Cover

Figure 1:
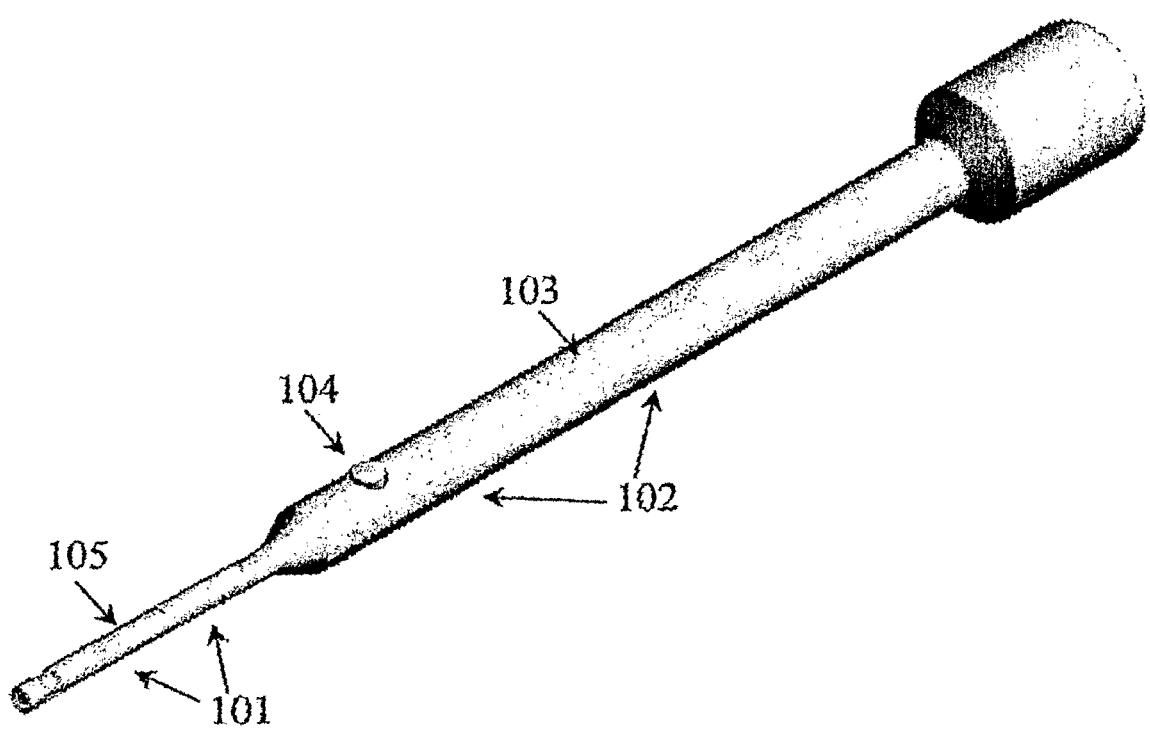
FIG. 1 illustrates an embodiment of the interior surface scanner according to the invention.
Figure 2:
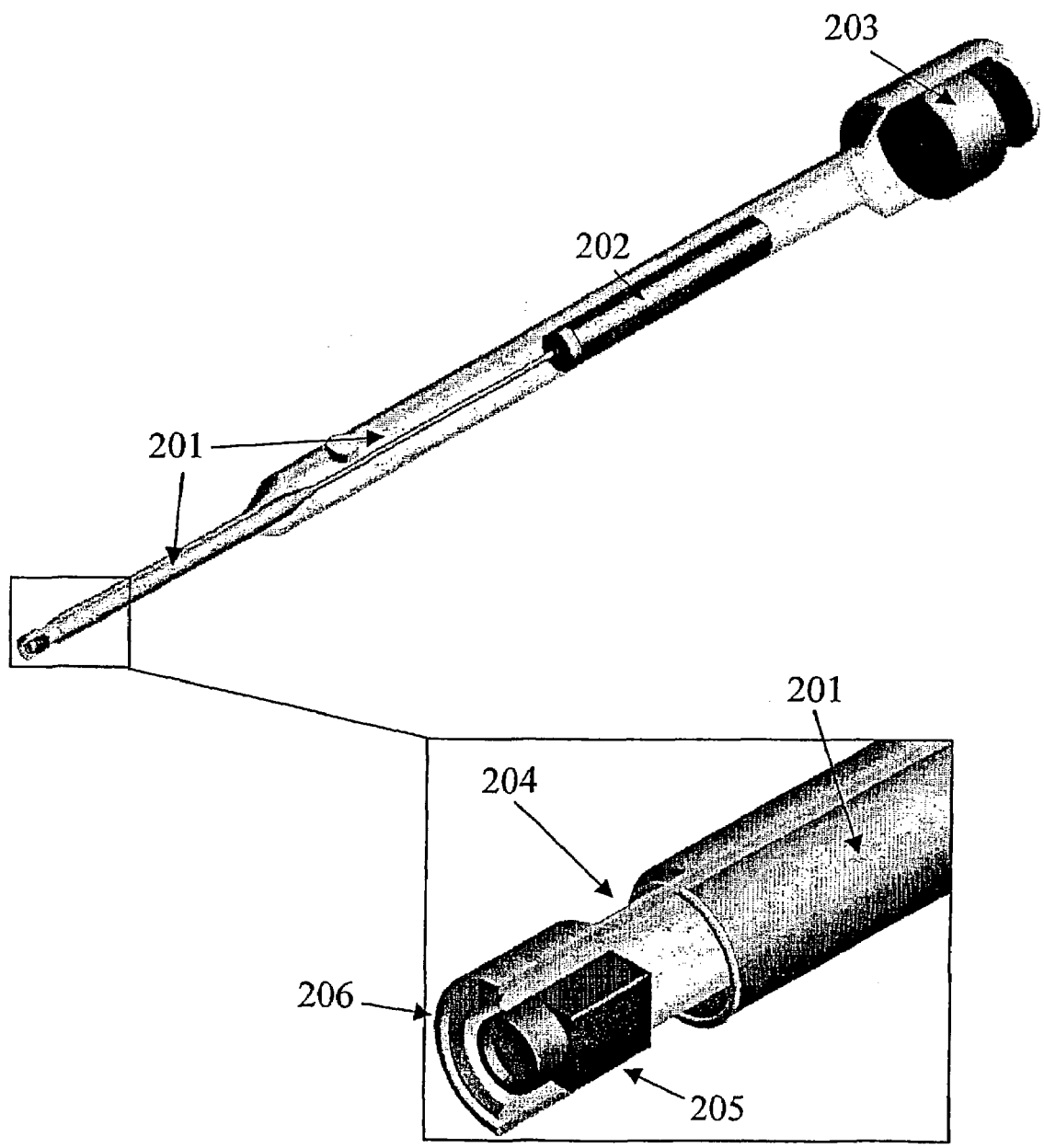
FIG. 2 shows a cross section of an embodiment of the interior surface scanner according to the invention.

In the design of the scanner show in FIG. 1 and FIG. 3 only the probe 101 is supposed to move into the cavity. The main objective of the design has been to minimise the width of this part, since it determines the minimal size of the cavity, which can be scanned. In general the width of the probe can be varied freely down to approximately 0.1 mm, e.g. the width can be 30, 20, 15, 10, 8, 6, 5, 4, 3, 2, 1 or 0.1 mm. However the final design is a trade-off between size, accuracy and mechanical stability. In general the application determines the desirable design.

In the case of scanning the human ear canal the width of the part is requested to be below 4 mm. FIG. 3 shows a scanner designed for scanning ear canals, where the width of the probe is 3.5 mm. The length of the probe can also be varied freely down to approximately 5 mm, e.g. the length can be 20, 35, 50, 100, 200, 300 or 500 mm. The length of the probe shown in FIG. 1 and FIG. 3 is 55 mm.

The rest of the scanner's cover is basically a handle. For optimal handling this part should preferably be 10-30 mm width and 100-150 mm long. The dimension can however be varied freely. As in FIG. 1 and FIG. 3 the width of the handle may be extended to make room for the components, e.g. the position sensor. The dimensions of this extension should however be minimised if the objective is to create the smallest and lightest scanner. The width and length of the extension shown in FIG. 1 and FIG. 3 is 40 mm and 30 mm, respectively. Note that larger light sources such as halogen spots may be moved to the extension.

In another embodiment of the scanner it is possible to rotate the probe 360 degrees around its axis. The advantage of this design compared to only rotating the mirrors and/or prisms as in FIG. 3 is that the motor can be placed in the handle. Likewise another embodiment comprises a linear drive, which is able to translate the probe along its axis. The scanner can also be mounted on a robot, a magnetic position system or another device, which is able to position the scanner with any orientation and position within its workspace.

The choice of material for the cover depends on the actual application, especially whether the probe needs to be rigid or flexible. Preferably the cover should be produced in stainless steel or from a material selected from a group consisting of alloy, aluminium, a plastic polymer, kevlar®, ceramics or carbon.

In some application it might be necessary to protect the components such as cameras, mirrors and/or prisms and lenses against dust and other dirt. In practise this is done by inserting a window of transparent material such as glass or a plastic polymer in the holes in front of the relevant components.

Miscellaneous Features

Other features in the preferred embodiment are a protector/collision detector, a scan button, and a disposable scanner cover. The protector consists of soft material such as rubber, silicone or a plastic polymer and ensures that the tip of the probe and the surface are not damaged in the case of a collision. In the case of scanning an ear canal it is crucial that the scanner does not damage the eardrum. In the case of very fragile surfaces, a collision detector adapted to measure the distance from the tip of the scanner to the bottom of the interior surface is added to the protector. When surfaces are scanned for which the scanner is subject to hygiene requirements, a disposable cover is desirable to minimize the need for cleaning. The disposable cover will usually only cover the probe or parts of it, but can be fit to the specific requirements. The scan button is used to start and stop the scan operation.

Processing

The acquired images are analysed real-time in a digital signal processor/microprocessor, which is placed in the scanner handle or in a separate processing box. The first step in the analysis of an image is to detect the light pattern in the image using a standard tracking algorithm. When the light pattern is known with sub-pixel precision, the corresponding 3D coordinates can be reconstructed using well-known projective geometry. A precise reconstruction of the 3D coordinates requires a very high quality of the camera and light calibration. The next step is to combine the 3D coordinates from different images acquired at the same or at different positions. The merging is simply performed by combining the individual points sets positioned with respect to their relative position. Finally the points are triangulated using a standard triangulation algorithm to form the final surface of the 3D model. The 3D model may then be transferred over a network to the destination for further use.

Uses of the Scanner

The scanner according to the invention is especially adapted for scanning interior surfaces, such as body cavities and other interior surfaces with narrow openings, into which light from an external scanner cannot enter due to occlusion effects.

Figure 13:
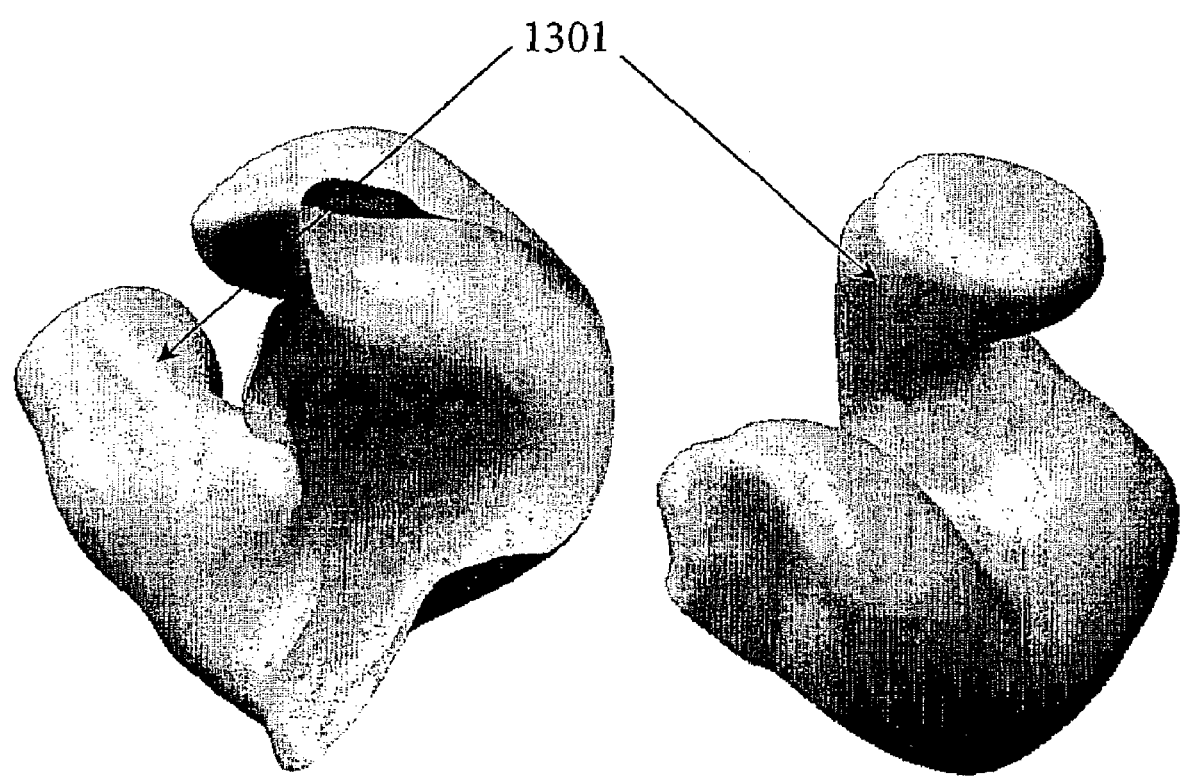
FIG. 13 shows a scan of an ear and an ear canal seen from two different views.

It is thus envisaged that the scanner is advantageous for scanning body cavities such as the internal surfaces of the ear, nose, mouth, teeth, stomach, lungs, alveoli, throat, rectum, vagina, veins, blood vessels, urinary tract. Scanning of teeth can be used in connection with correction of teeth and manufacture of dental implants. Scanning the blood vessels may be useful in connection with surgery. Scanning the vagina can be used in connection with pregnancy and delivery and also for measuring and modelling an individually adapted diaphragm. FIG. 13 shows a scan of the interior surface of an ear and an ear canal 1301.

The scanner can also be used for industrial purposes such as for scanning internal surfaces of engines, fuel canals, bore, internal thread, pipes, tubes and containers. In this way the exact dimensions (volume and/or cross section and/or location of features) of the devices can be measured. When using a scanner with a position sensor this can be done more precisely than any of the known scanners. Furthermore, the present scanners are not sensitive to small deviations in the orientation of the axis of the scanner with respect to the axis of the object being scanned.

Another use is for archaeological purposes such as for scanning internal surfaces of jars, skulls and other archaeological items.

Furthermore, the scanners are very useful in industrial design especially in connection with computer assisted 3D modelling.

Scanning the Ear

A possibility according to the invention is to scan the ear canal directly. This can be done by building the components of the scanner into an apparatus, which can be inserted into the ear of the patient. Embodiments of this scanner are shown in FIG. 11. Preferably, the light source, e.g. the laser, and the camera are located outside the ear. The laser light can be carried into the scanner by light guides 201, and similarly, the reflected signals can be carried to a camera by another light guide 801. The scanner also consists of a position sensor 203, which measures the relative position of the scanner with respect to the object. During the scan, the scanner preferably rests on the edge of the ear canal, most preferably in those places where bones are closest to the skin surface. This is in order to obtain the highest stability and is very important, since the scanner itself works with an accuracy less than 0.05 mm. The length of the ear canal can be scanned by moving the scanner in or out and record a series of overlapping images of the ear canal. The scanner may comprise only one laser source and one camera as the one shown in the left of FIG. 11. In that case the scanner has to rotate while the camera records images. Preferably, the scanner comprises multiple laser sources such as four as shown in the scanner in the right part of FIG. 11. The presence of multiple laser sources and cameras removes the need for rotation of the scanner in the ear canal. In the laser scanner disclosed in FIG. 11, the laser source or sources project a ray of laser light on the surface of the ear canal.

Another type of ear canal laser scanner is shown in FIG. 12. Here the laser light is projected as laser sheets producing a laser contour on the surface of the ear canal. Thereby, more rapid scanning can be performed compared to the above laser scanner. In the scanner shown in the right part of FIG. 12, four laser sheets and four cameras are present. Thereby the laser sheets cover the whole circumference and rotation of the scanner is not required.

The same types of variation of the ear canal scanner can be used as in other cases of three-dimensional scanners according to this invention. Thus, preferably the scanner comprises at least two cameras, more preferably 4 cameras such as for example 6 cameras. Likewise, there may be several laser sources such as for example 2 lasers creating laser sheets with an offset of 180°, preferably 3 laser sheets with an offset of 120°, or 4 laser sheets with an offset of 90°.

Prior to scanning, the patient's ear must be rinsed to remove cerumen. In some cases it may also be advantageous to treat the surface of the ear canal if the appearance is too glossy.

One scan can be performed in less than 1 minute, and it is thus possible to record a number of scans of one ear, and ask the patient to deliberately vary the size of the ear canal by swallowing, yawning, chewing, and drinking. In this way a series of scans of the ear canal can be recorded and the magnitude of the variation of the patient's ear canal can be detected. In the end it is possible to superimpose these scans on one another to create a model, which will fit the patient's ear under all conditions. Such a model is naturally made as a compromise between the different sizes of the ear canal.

The improved fit of the hearing aid shells according to the present invention compared to prior art hearing aid shells means that the frequent problem of acoustic feedback in hearing aids is minimised. The direct scanning of the ear significantly reduces the production cost of hearing aids, since the impressions used today are rendered superfluous. The removal of the impression removes the handling and mailing cost and cuts down the production time and improves flexibility.

Ear Model

Currently hearing aids are created in a silicon mould, made with an ear impression.

It is possible to scan and create very detailed and accurate copies of ear impressions with the developed system as described in co-pending PCT/DK01/ ("Object and method for calibration of a three-dimensional light scanner", filed by 3-Shape on 24. Aug. 2001).

Apart from hearing aids, other devices could also be inserted into a shell made to fit the ear canal of an individual. Such devices that could advantageously be incorporated into a shell manufactured according to the disclosed method include mobile phones, communication devices, loud speakers, tinnitus masking devices, or devices recording vibrations in the skull and transforming these into an audio signal.

Devices that may be incorporated into a shell in the ear also comprise devices related to Man Machine Interface (MMI) products, such as custom made ear microphone/receivers that enable reliable and clear communication even in the noisiest environments, or products related to wireless internet applications.

Speech not only creates sound waves, it also generates vibrations within the skull of the speaker. These vibrations can be picked up in the ear (they may be picked up other places too, but by far the most convenient method is to do it in the ear). In one piece, a device thus may comprise a microphone to pick up the speech of the person wearing it, and a loudspeaker to transmit the speech of the communication partner. It is important that such devices are made to fit the ear.

The devices based detection of vibration instead of sound can be used in the noisiest environments, since they only pick up the speech of the wearer and they allow for quiet communication, since the speaker can speak with a low voice when needed. The devices allow for completely hand-free communication.

Such a device is naturally also devoid of any kind of acoustic feedback if manufactured using the present invention.

Calibration

The precision of the light sources and cameras is very high today and so is that of the software developed to detect the intersection of the light sheet with the object and convert the two-dimensional data to three-dimensional co-ordinates. Therefore differences in precision and hence improvement of the precision primarily resides in the calibration of the systems. Recall that precision is of utmost importance in many applications.

Figure 10:
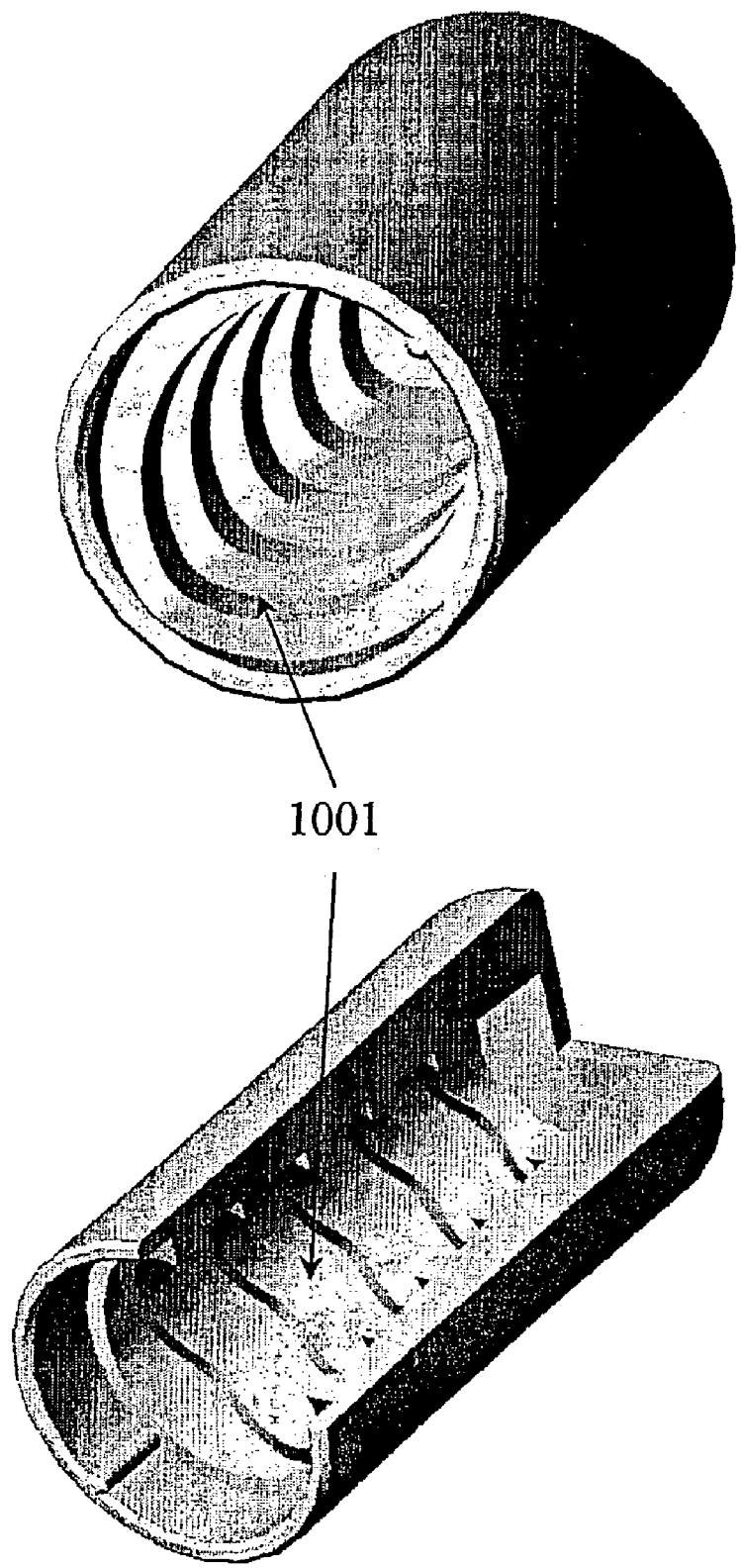
FIG. 10 shows an embodiment of a hollow calibration object used for calibration of the camera and light sources. Note the symmetric 3D object feature curves on the object, which are utilised in the calibration.

To obtain the highest precision both the light pattern and the camera need to be calibrated. Preferably the calibration should be performed using a calibration object with symmetrical 3D object feature curves and the corresponding methods as described below and in co-pending PCT/DK01/ ("Object and method for calibration of a three-dimensional light scanner", filed by 3-Shape on 24. Aug. 2001). The main advantage of this type of calibration objects is that the light pattern can be calibrated independently of the calibration of the camera. An embodiment of the hollow calibration object used for calibration of the scanner is shown in FIG. 10. Note the symmetric 3D object feature curves 1001 on the calibration object, which are utilised in the calibration.

Preferably, a light pattern is projected onto the calibration object to produce 2D image feature curves in the acquired images.

When preferred, the image feature curves may be determined using the Hough transformation, filter search, max intensity, threshold, centre of gravity, derivatives or other procedures.

The image feature coordinates are found as the intersection between image feature curves. These intersections could be seen in the images as corners or sharp edges of the image feature curves. The image feature co-ordinates may be found as the intersection between the image feature curves such as the intersection between two $n^{th}$ order curves, as the intersection between two first order curves, as the intersection between two second order curves, as the intersection between two third order curves, as the intersection between a fist order curve and a second order curve, as the intersection between a first order curve and a third order curve, or as the intersection between a second order curve and a third order curve or as the intersection between any other possible combination of curves.

Preferably, the calibration method further comprises plotting of a mathematical combination of image feature points or features derived from these points against the angle of rotation or the translation of the calibration object. By plotting this function and optionally estimating a mathematical function describing the relationship between the function of an image co-ordinate and the angle of rotation or the translation, estimation of the light parameters and angle or rotation and/or translation becomes especially precise. The method may further comprise determination of the mean plane of symmetry in the plot.

The mean plane of symmetry can be determined by calculating the mean angle of rotation/mean translation for pairs of image feature points having the same value in the mathematical combination. Doing this produces multiple estimates for the encoder offset and light pattern displacement allowing also for the estimate of the laser sheet angle.

Light pattern calibration may also comprise selecting symmetric points, plotting of the rotation angle and/or the translation for the first point against the difference in the rotation angle and/or the translation between the two symmetric point, deriving mathematical formula for the plotted lines and estimating the light pattern parameters.

Alternatively, mathematical formulas can be derived for the curves, which appear in some of the plots of the mathematical combination as a function of the angle of rotation or the translation. Given these curves and the corresponding formulas, the encoder offset, the light pattern displacement and the light pattern angle can be estimated.

Preferably, light pattern co-ordinates of the 3D object feature curves are estimated corresponding to a discrete number of values of angle of rotation and/or translations. These values should preferably cover the whole circumference and/or length of the calibration object.

2D co-ordinates of the 3D object feature curves corresponding to a discrete number of values of angle or rotation and/or translation may be calculated from mathematical functions determining the 3D object feature curves. In order to determine the calibration parameters such as camera position, camera orientation, and camera optic parameters, pairs of 2D light pattern co-ordinates are compared to calculated 2D co-ordinates for a discrete number of values of angle or rotation and/or translation. This comparison preferably comprises using the Tsai or the Heikkilä algorithm. The advantage of the Tsai and the Heikkilä algorithm in this context is that it provides rapid and precise estimation of the calibration parameters such as radial lens distortion.

Alternative methods for calibration comprise direct linear transformation and direct non-linear matrix transformation optionally in combination with an optimisation procedure such as least squares means to minimise the error. In these cases initial calibration parameters may be estimated to facilitate the convergence of the parameters during optimisation.

To improve calibration precision outliers may be excluded from the calibration. Outliers can e.g. be identified in the plot of the mathematical combination of image feature co-ordinates against the angle of rotation/the translation or by back projection of co-ordinates after an initial calibration.

2% of the feature points deviating most from the back-projected 2D image feature curves may be excluded from the calibration or at least 3%, such as at least 5%, for example at least 10%, for example at least 12%, such as at least 15% for example at least 20, preferably at least 25%, for example at least 30%, more preferably at least 33% may be excluded to improve calibration precision.

In order to cover the whole circumference of the calibration object the discrete number of values for angle of rotation/ translation may be at least 100, preferably at least 240, for example at least 500, such as at least 750, for example at least 1000, such as at least 1200, for example at least 1500, such as at least 1800, for example at least 2000, such as at least 2400, for example at least 3000, for example at least 3600, such as at least 4200. The higher the discrete number of values of angle of rotation/translation, the higher the calibration precision.

The highest calibration precision is obtained when using a rigid setup, which comprises mounting the calibration object onto mounting means.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A scanner for three-dimensional scanning of interior surfaces to determine a shape thereof comprising:
    at least one light source adapted to create and project structured light producing a pattern on the interior surface of an object;
    at least one camera adapted to record 2-D images of the pattern;
    a data processor adapted to convert information from said 2-D images into 3-D real world coordinates corresponding with a shape of said interior surface;
    at least one position sensor having an emitter part and a receiver part, one of said emitter and receiver parts being provided on the scanner and the other of said emitter and receiver parts being provided on the object to be scanned, said position sensor being adapted to provide the relative position and orientation of the scanner relative to said surface being scanned to enable combining of the individual scans when the scanner and the object are moved relative to one another during successive scans;
    the point of emission of light as well as the point of accumulation of reflected light for the camera being located on a probe having an axis;
    the at least one light source and the at least one camera being adapted to perform a scan 360° around the axis without rotation of said probe; and
    the probe being adapted to be entered into a cavity.

2. The scanner according to claim 1 wherein the probe is rigid.

3. The scanner according to claim 1, wherein the probe is flexible.

4. The scanner according to claim 1, wherein the probe has a diameter or cross section of less than 30 mm.

5. The scanner according to claim 1, wherein the probe has a diameter or cross section of less than 20 mm.

6. The scanner according to claim 1, wherein the probe has a length of up to 500 mm.

7. The scanner according to claim 1, wherein the probe is made from a material selected from the group consisting of an alloy, aluminum, kevlar, a polymer, ceramics, and carbon.

8. The scanner according to claim 1, wherein the probe is made from a material selected from the group consisting of polymer.

9. The scanner according to claim 1, wherein the pattern of structured light comprises at least one ray of light forming at least one point on the surface.

10. The scanner according to claim 9, wherein the pattern includes at least 10 rays.

11. The scanner according to claim 1, wherein the at least one light source is adapted to create and project rectangular shaped rays forming a distorted checkerboard pattern on the interior surface.

12. The scanner according to claim 1, wherein the pattern of structured light includes at least one plane of light forming at least one contour on the surface.

13. The scanner according to claim 1, wherein the pattern of structured light comprises at least one cone of light.

14. The scanner according to claim 1, wherein the at least one light source includes a laser, variable output-powered laser, laser emitting diode (LED), a halogen spot or another spotlight.

15. The scanner according to claim 1, wherein the light source has a cross section perpendicular to the direction of emitted light of less than 5 mm.

16. The scanner according to claim 1, including at least two light sources.

17. The scanner according to claim 1, including at least five light sources.

18. The scanner according to claim 1, whereby the light source intensity is varied depending on the surface and/or colour of the object to be scanned.

19. The scanner according to claim 18, whereby the light source intensity is determined automatically using automatic light source intensity calibration.

20. The scanner according to claim 1, wherein the at least one light source is arranged such that structured light is emitted in different directions covering 360° around the probe.

21. The scanner according to claim 1, wherein the at least one camera comprises a sensor array.

22. The scanner according to claim 1, wherein the at least one camera comprises a CCD.

23. The scanner according to claim 1, wherein the at least one camera comprises a CMOS.

24. The scanner according to claim 1, wherein the light detecting component of the camera has a cross section in a direction perpendicular to the direction of incident light of less than 10 mm.

25. The scanner according to claim 1, wherein the camera comprises an array of at least 125*125pixels.

26. The scanner according to claim 25, wherein a cross section of a pixel is less than 100 μm.

27. The scanner according to claim 1, wherein the at least one camera is colour sensitive.

28. The scanner according to claim 1, further comprising a filter in the light path between the object surface and the camera being adapted to filter light from other light sources than the individual light sources of the scanner.

29. The scanner according to claim 1, including at least two cameras.

30. The scanner according to claim 1 further comprising a plurality of light sources and a plurality of cameras adapted to perform said scan 360° around the axis without rotation of said probe.

31. The scanner according to claim 1, wherein said position sensor includes a receiver located on said scanner and a transmitter located on the object being scanned.

32. A method for scanning interior surfaces to determine a shape thereof comprising the steps of;
    i) entering a probe shaped scanner having an axis into a cavity;
    ii) creating and projecting structured light from a first point on the probe producing a pattern on an interior surface of an object and, at a second point of the probe, recording 2D images of the pattern reflected from the interior surface to perform a scan 360° around the axis of the probe without rotation of said probe;
    iii) determining 2D coordinates of the 2D images of the pattern;

iv) determining the relative position and orientation of the scanner relative to said surface being scanned for enabling combining of the individual scans when the scanner and the object are moved relative to one another during successive scans with at least one position sensor having a receiver part and an emitter part, one of said receiver and emitter parts being provided on the scanner and the other of said receiver and emitter parts being provided on the object to be scanned; and v) converting a series of said 2D images into 3D real world coordinates of the interior surface corresponding with the shape thereof.

33. The method according to claim 32, wherein step ii) is performed using
at least one light source and at least one camera that are adapted to perform the scan 360° around the axis.

34. The method according to claim 32, further comprising, before steps i) through v), calibrating the scanner by adjusting calibration parameters thereof, said step of calibrating including:
scanning a three dimensional calibration object having at least one plane of symmetry and whereby at least part of at least one 3D object feature curve of each symmetric part is a continuous curve;
determining image feature coordinates being representations of at least one pair of 3D object feature curves for each of a discrete number of values of an angle of rotation and/or a translation, a pair consisting of one 3D object feature curve in each symmetric part of the calibration object; and
adjusting the calibration parameters based on the image feature coordinates to fit the calibration object.

35. The method according to claim 34, whereby a light pattern is projected onto the calibration object producing 2D image feature curves.

36. The method according to claim 35, whereby the 2D image feature curves are determined using the Hough transformation.

37. A method for 3D modelling and production including obtaining 3D real world coordinates of an interior surface of a cavity to determine a shape thereof comprising the steps of:
i) entering a probe shaped scanner having an axis into a cavity;
ii) creating and projecting structured light from a first point on the probe producing a pattern on an interior surface of an object and, at a second point of the probe, recording 2D images of the pattern reflected from the interior surface to perform a plurality of successive scans 360° around the axis of the probe without rotation of said probe;
iii) determining 2D coordinates of the images of the pattern;
iv) determining the relative position and orientation of the scanner relative to said surface during said plurality of successive scans with at least one position sensor having a receiver part and an emitter part, one of said receiver and emitter parts being provided on the scanner and the other of said receiver and emitter parts being provided on the object to be scanned;
v) converting a series of said 2D images into a plurality of 3D real world coordinates of the interior surface;
vi) combining said plurality of 3D coordinates from images taken during said successive scans with respect to relative position of said scans as determined by said position sensor to create a 3D model corresponding with the shape of said cavity; and
vii) creating a piece adapted to fit into the cavity.

38. The method according to claim 37, wherein production includes at least one of milling, 3-dimensional printing, stereo lithography, selective laser sintering, laminated object modelling, inkjet modelling, fused deposition modelling, and nano-printing.

39. The method according to claim 37, wherein 3D modelling includes computer assisted modelling of the scan data prior to production.

40. The method according to claim 37, wherein said cavity is an ear canal and step vii) includes producing a hearing aid shell adapted to house a device.

41. The method according to claim 40, wherein step vi) includes superimposing multiple scans of a same portion of said ear canal using data from said position sensor.

42. The method according to claim 41, wherein step ii) includes performing said plurality of successive scans while a size of said ear canal is varied by physical movements of the person whose ear canal is being scanned, said physical movements including at least one yawning, swallowing, eating and drinking.

* * * * *

UNITED STATES PATENT AND TRADEMARK OFFICE
CERTIFICATE OF CORRECTION

PATENT NO. : 7,625,335 B2
APPLICATION NO. : 10/344703
DATED : December 1, 2009
INVENTOR(S) : Deichmann et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 453 days.

Signed and Sealed this

Twenty-sixth Day of October, 2010

David J. Kappos
*Director of the United States Patent and Trademark Office*